United States Patent
Bauer

(10) Patent No.: US 12,036,140 B2
(45) Date of Patent: Jul. 16, 2024

(54) TEXTILE PART

(71) Applicant: medi GmbH & Co. KG, Bayreuth (DE)

(72) Inventor: Patrick Bauer, Auerbach (DE)

(73) Assignee: MEDI GMBH & CO. KG, Bayreuth (DE)

( * ) Notice: Subject to any disclaimer, the term of this patent is extended or adjusted under 35 U.S.C. 154(b) by 115 days.

(21) Appl. No.: 17/064,143

(22) Filed: Oct. 6, 2020

(65) Prior Publication Data

US 2021/0121311 A1    Apr. 29, 2021

(30) Foreign Application Priority Data

Oct. 24, 2019  (EP) .................................. 19204988

(51) Int. Cl.
| | |
|---|---|
| *A61F 13/01* | (2024.01) |
| *A61F 5/01* | (2006.01) |
| *A61F 5/048* | (2006.01) |
| *A61F 13/00* | (2006.01) |
| *A61F 13/08* | (2006.01) |

(Continued)

(52) U.S. Cl.
CPC ............ *A61F 5/0102* (2013.01); *A61F 5/048* (2013.01); *A61F 13/00987* (2013.01); *A61F 13/01* (2024.01); *A61F 13/01017* (2024.01); *A61F 13/01029* (2024.01); *A61F 13/08* (2013.01); *A61F 2005/0132* (2013.01); *B29C 65/08* (2013.01); *B29C 66/729* (2013.01)

(58) Field of Classification Search
CPC .......... A61F 13/00004; A61F 13/00029; A61F 13/00021; A61F 13/00; A61F 13/00987; A61F 13/00017; A61F 13/00008; A61F 5/024; A61F 5/30; A61F 5/32; A61F 5/34; A61F 2013/0028; A61F 2013/00468; A61F 13/107; A61F 13/108; A61H 39/04
USPC .................................. 602/75, 76, 53, 41, 60
See application file for complete search history.

(56) References Cited

U.S. PATENT DOCUMENTS

| | | | |
|---|---|---|---|
| 5,792,176 A * | 8/1998 | Chang ................... | A61H 39/04 606/189 |
| 7,527,602 B2 * | 5/2009 | Weaver, II ........... | A61F 13/108 602/61 |
| 9,393,147 B2 | 7/2016 | Scheuermann | |

(Continued)

FOREIGN PATENT DOCUMENTS

| | | |
|---|---|---|
| DE | 102010026680 A1 | 1/2012 |
| DE | 102011118617 A1 | 5/2013 |
| EP | 2779963 B1 | 2/2019 |

OTHER PUBLICATIONS

Collins Dictionary, "textile," https://www.collinsdictionary.com/us/dictionary/english/textile.*

*Primary Examiner* — Victoria Hicks Fisher
(74) *Attorney, Agent, or Firm* — LUCAS & MERCANTI, LLP; Klaus P. Stoffel

(57) ABSTRACT

A textile part, in particular a textile orthopedic aid, having a textile main panel as well as at least one functional element from plastics material which is disposed on the main panel, wherein at least one planar cover element which engages only in portions across the functional element disposed in the main panel and which also extends across the main panel is provided, wherein the cover element is connected to the main panel and/or the functional element, and the functional element is connected to the main panel in a materially integral manner.

11 Claims, 3 Drawing Sheets

(51) Int. Cl.
*B29C 65/00* (2006.01)
*B29C 65/08* (2006.01)

(56) References Cited

U.S. PATENT DOCUMENTS

| | | | |
|---|---|---|---|
| 2011/0015557 A1* | 1/2011 | Aali | A61F 13/00068 |
| | | | 602/56 |
| 2014/0257154 A1 | 9/2014 | Brown | |
| 2014/0276300 A1 | 9/2014 | Reinhardt | |
| 2015/0335457 A1* | 11/2015 | Bauer | A61F 5/0123 |
| | | | 602/26 |
| 2019/0142620 A1 | 5/2019 | Omarsson | |

* cited by examiner

TEXTILE PART

CROSS-REFERENCE TO RELATED APPLICATIONS

The present application claims priority of EP 19 204 988.0, filed Oct. 24, 2019, the priority of this application is hereby claimed and this application is incorporated herein by reference.

BACKGROUND OF THE INVENTION

The invention relates to a textile part, in particular a textile orthopedic aid, comprising a textile main panel as well as at least one functional element from plastics material which is disposed on the main panel.

Such a textile part, as is known from EP 2 779 963 B1, for example, is embodied as a sleeve or as a bandage, for example, and serves for bearing on a body of a wearer. The textile part has a textile main panel on which at least one functional element from plastics material is disposed, said functional element being embodied as, for example, an elongate splint or as a joint or similar. This functional element serves for imparting to the textile part a specific functional property which is helpful to the wearer, thus acts in a stabilizing or reinforcing manner, for example, so as to protect in relation to mechanical influences and similar on that part of the body that is engaged across by the textile part.

Besides the possibility of incorporating such a functional element in a pocket which is preferably configured on the main panel by way of knitting technology, thus for example of pushing a stabilizing rod into a corresponding elongate pocket, for example, it is also known for the functional element to be fixed to the main panel by way of a materially integral connection, thus a welded connection. This is known, for example, from EP 2 779 963 B1 where a functional element is welded to the main panel, for example a bandage, by way of a carrier element which is laminated with plastics material. The functional element per se is applied to the carrier element, this taking place, for example by over-molding or back-molding, in a first process step. This combined component in a second process step is thereafter placed on the bandage and welded exclusively in the region of the carrier element, the latter being wider than the functional element, this taking place by fusing the plastics-material coating of the carrier element. The functional element per se in this design embodiment is not connected to the main panel but connected to the latter merely by way of the carrier element, this leading to potential deficiencies arising in the functionality of the functional element since the properties of the latter, for example stabilizing properties, are not transmitted directly to the main panel. Moreover, the production procedure is also complex since the combined component composed of the functional element and the carrier element has initially to be produced in a first process step, whereupon the application of this combined component to the main panel takes place only in a second process step.

SUMMARY OF THE INVENTION

The invention is thus based on the object of specifying a textile part which is improved in comparison to the above.

In order for this object to be achieved it is provided according to the invention in a textile part of the type mentioned at the outset that at least one planar cover element which engages only in portions across the functional element disposed on the main panel and which also extends across the main panel is provided, wherein the cover element is connected to the main panel and/or the functional element, and the functional element is connected to the main panel in a materially integral manner.

A very simple construction which enables the functional element to be able to transmit the functional properties thereof in the best possible manner to the main panel, on the one hand, but also that reliable fixing of the functional element on the main panel as well as a corresponding partial covering of the functional element that protects and covers the functional elements, on the other hand, is provided. According to the invention, the functional element is connected directly to the main panel in a materially integral manner, this taking place by way of a corresponding welded connection in that the functional element composed of plastics material is locally fused at the interface toward the textile main panel such that the fused plastics material wets the textile knitted fabric, optionally slightly penetrates the latter, and when curing fixedly connects to the latter. This guarantees optimal transmission of function from the functional element to the knitted panel as well as fixing in the best possible manner. Moreover provided is a planar and preferably flexible cover element which engages only in portions across the functional element and which also extends across the main panel and which is fixed either to the main panel, to the functional element, or to both. This cover element covers the functional element as well as the fastening plane of the latter toward the main panel, thus protecting said fastening plane in relation to any potential damage, this being advantageous in terms of the durability of the material integral connection.

In comparison to the known prior art, such as in particular EP 2 779 963 B1, the textile part according to the invention is thus distinguished by a very simple construction since a carrier element is dispensed with by virtue of the functional element being welded directly to the textile main panel. Consequently, no complex production step is required for a corresponding combined component; rather, the functional element is supplied directly to the main panel. An optimal transmission of function to the main panel and thus also to the wearer of the textile part is possible by virtue of this direct application, while a concealed disposal of the fastening plane of the functional element is guaranteed by way of the cover element.

Three design embodiments which are to be differentiated are thus in principle conceivable according to the invention. According to a first alternative of the invention, the cover element can be connected to the main panel and the functional element. Three fastening planes are provided here, so to speak, specifically the connection between the cover element that engages across the main panel and the main panel and the functional element, on the one hand, and the materially integral connection between the functional element and the main panel, on the other hand. The cover element is consequently fixed twice. If the cover element is equipped with a corresponding content of plastics material, as is particularly preferably provided, thus for example with a plastics material lamination, the connection between the cover element and the main panel can thus also be in a materially integral manner; this means that the connection to the functional element as well as the connection to the main panel is materially integral, this being associated with the particular advantage that all three connections can be established in a single process step in that the regions on the cover element and on the functional element are fused by an input of energy such that a material integral fuse connection between the cover element and the main panel as well as the functional element is established on the one hand, and between the functional element and the main panel on the other hand.

A second alternative provides that the cover element is connected only to the functional element and lies loosely above the main panel. In this design embodiment of the invention, the fastening regions or fastening planes between the cover element and the functional element and between the functional element and the cover element, when viewed from the main panel, lie behind one another, so to speak. The cover element in those regions where said cover element is engaged across by the functional element is connected to the functional element either in a fully circumferential manner or across the entire area, respectively, or only locally. This connection can particularly preferably likewise be material integral since the functional element, as described, is from plastics material and accordingly can be fused by an input of energy such that a materially integral connection to the cover element is established, irrespective of how the latter is embodied or from which material the latter is, respectively, as long as said cover element guarantees corresponding wetting and thus a materially integral connection. Of course, there is also the possibility of equipping the cover element per se with a corresponding content of plastics material, for example with a plastics-material lamination, such that said cover element per se can be locally fused by an input of energy in order for the materially integral connection to be implemented. The second connection plane in which the functional element is connected to the main panel in a materially integral manner is in this instance below said first connection plane, so to speak. Here too, there is thus the possibility of configuring both connections in a single process step by way of a single input of energy and by fusing the corresponding components in the relevant regions.

A third alternative of the invention finally provides that the cover element is connected only to the main panel and lies loosely above the functional element. In this alternative of the invention, two fastening regions or fastening planes which lie beside one another are provided, so to speak, specifically the fastening regions of the cover element on the main panel, on the one hand, and the fastening region of the functional element toward the main panel, on the other hand. The cover element here too can preferably be equipped with a content of plastics material so as to in turn implement a welded plastics-material connection toward the main panel here too, thus a materially integral connection such as is also provided between the functional element and the main panel. This enables the fastening of all components to one another in a single process step by way of a single input of energy also in the case of this third variant of the invention.

It is however to be pointed out here already that, as far as the connection between the cover element and the main panel is concerned, a form-fitting connection may also be provided instead of a materially integral connection, such as can be established by sewing the cover element to the main panel while using a corresponding sewing thread, for example, or by riveting. This applies to all exemplary embodiments or variants of embodiments of the invention disclosed.

The cover element per se in a refinement of the invention can have a through-hole, for example an elongate slot, wherein the cover element in this case is embodied in the manner of a rectangular, frame-type component, for example, which engages across the functional element which is disposed in the region of the slot. The design embodiment herein can be in such a manner that the functional element runs behind the through-hole. The functional element in this case is embodied, for example, as a flat stabilizing stiffener which is welded to the main panel and which is engaged across by the cover element which is fastened to the main panel and to the functional element, for example, preferably welded to said main panel and said functional element. The functional element can be seen through the slot such that the type of functional element can be identified on the one hand; on the other hand, this can also be utilized for design reasons, for example when the functional element has a very conspicuous color which deviates from the color of the main panel, or similar.

Alternatively, the cover element can also run so as to be flush with the functional element engaging in the through-hole. In this case, the functional element has a T-shaped cross section, for example, wherein said functional element by way of the transverse leg is welded to the main panel, and the relatively short longitudinal leg which extends from the transverse leg extends into the through-hole of the cover element but runs so as to be substantially flush with the free side of the cover element.

In a third alternative, the functional element having a T-shaped cross-sectional design can finally also penetrate the through-hole, thus project from the latter by a few millimeters or more. This means that various design embodiments are provided in terms of the geometry of the functional element as well as of the geometric linking of the latter, or of the transition of the latter toward the cover element, respectively.

It is furthermore preferable for the functional element on one or a plurality of sides to have a laterally projecting fastening portion which is engaged across by the cover element and is connected to the main panel by way of said cover element, wherein the raised portion of the functional element that adjoins the fastening portion extends into or through the through-hole. As has already been described above, it is conceivable for the functional element to have a T-shaped cross section. In this case, two lateral fastening portions which are engaged across by the cover element are provided. However, an L-shaped cross section of the functional element, having only one fastening portion which is engaged across by the cover element, is also conceivable. The fastening portion or fastening portions serve for connecting the functional element to the main panel, wherein the functional element in the region adjacent to the fastening portion or fastening portions can also be welded to the main panel, thus be welded across the entire bearing face.

The cover element per se can preferably be connected to the main panel and/or the functional element in a materially integral manner, that is to say that a welded connection is preferably established here too. This can take place either in that the cover element per se is equipped with a corresponding content of plastics material which can be fused, for example having a laminated plastic film or similar, or that a fusible intermediate tier may be provided, this yet to be discussed hereunder. This is particularly expedient in order for a materially integral connection to the main panel to be established. A corresponding plastic finish of the cover element is not mandatory for a materially integral connection to the functional element which is already composed of plastics material, but such a corresponding plastic finish may likewise be provided. Alternatively or optionally additionally, there is however also the possibility of connecting the cover element in particular to the main panel in a form-fitting manner, thus sewing said cover element, for example, this likewise leading to a fixed connection.

One advantageous refinement of the invention provides that the cover element connected only peripherally to the main panel, while forming an accessible pocket, is open on at least one side. The cover element in this design embodiment, when viewed laterally, extends relatively far away from the functional element and in the peripheral regions, with the exception of one side or a corresponding lateral portion, is fixedly welded and/or sewn to the main panel. The opening enables the functional element, thus a stabilizing element, for example, to be pushed into the pocket and then to be fixed proximal to the main panel, wherein additional fixing of the cover element to the functional element is also possible here, for example again by way of a materially integral connection which is simultaneously established. Thus the cover element here can first be sewn to the main panel, for example, whereupon the push-fitting and fixing of the functional element takes place by welding.

As has already been described, it is possible for the cover element to be provided with a fused or fusible, respectively, coating which establishes a materially integral connection and which by an input of energy is fused for generating a materially integral connection to the main panel and/or the functional element. This means that the cover element per se is equipped with a corresponding content of plastics material, for example in the form of a melt thread which can be fused by an input of energy such that the materially integral adhesive connection is enabled. Alternatively, a fused intermediate tier which establishes the materially integral connection, thus a corresponding plastic film or similar which when fused establishes a materially integral connection to the cover element on the one side as well as to the main panel or the functional element on the other side, can also be provided between the cover element and the main panel and/or the functional element. Both design embodiments, thus the lamination of the cover element by way of the plastics material tier, on the one hand, and the intervention of the intermediate tier, on the other hand, enable only the non-processed cover element face to be seen from the external side of the textile part, this means that the plane of the materially integral connection is not visible since the cover element per se is specifically not fused but only the corresponding plastic finish of said cover element or the intermediate tier.

Alternatively, it is of course also conceivable that the cover element per se is composed of a material that establishes the materially integral connection or contains such a material, that is to say that the cover element per se, for example in the form of a plastic film, is locally fused in order to establish the materially integral connection.

The cover element per se is preferably a planar element to which end a textile is particularly suitable. Said textile is of course preferably non-transparent since said textile as a cover element is after all intended to cover the functional element in portions and corresponding materially integral connection regions. A hook-and-loop capable textile can preferably also be used, said textile enabling even further elements to be fixed externally on the cover element if required, or said textile per se having a hook contact face by way of which said textile can be connected, thus fixed in the manner of a hook-and-loop fastener, to the main panel in order for a form-fitting connection to be established, for example. A velour, or a hook-and-loop velour, is particularly preferable herein, this being a medium-fine warp-knitted material in which individual filaments of thread floats by way of a finishing process such as raising, in particular on a roller raising machine, are lifted and solidified so as to form loops in order to be hook-and-loop capable. The invention is however not limited to the use of such a velour; rather, each textile, or each textile layer, respectively, in the form of a woven fabric, a warp-knitted fabric, or a circular or flat knitted fabric, can be used as a cover element. As an alternative to the use of a textile, the use of a cover element in the form of a plastic film is however also conceivable, wherein a plastic film also has a corresponding flexibility in order for the optionally present movements of the main panel or of the functional element to which the plastic-film cover element is connected to be replicated.

The main panel per se is expediently a knitted panel, in particular a compressive knitted panel, which by incorporating one or a plurality of elastic threads, in particular weft threads, has a defined compressive property, consequently establishes a defined pressure on the tissue or the portion of the body, respectively, that said knitted panel engages across. In terms of the design embodiment of a textile part having compressive properties, reference is to be made, for example, to the definitions in "Quality Assurance RAL-GZ387/1 Medical Compression Stockings" and "Quality Assurance RAL-GZ387/2 Medical Compression Arm Hosiery) of Gütezeichengemeinschaft medizinische Kompressionsstrümpfe e. V (Quality Seal Association of Medical Compression Hosiery), where corresponding quality and testing guidelines are stated for medical compression stockings (and arm hosiery) which can likewise be a textile part according to the invention.

The materially integral connection, as has been discussed, is a welded plastics-material connection. Said connection can be established by high-frequency welding or ultrasonic welding, that is to say that energy is introduced into the material to be fused by way of high-frequency or ultrasonic vibrations, respectively, heat consequently being generated such that the plastics material, whether the functional element per se, a plastic finish of the cover element, an intermediate tier, melts at least locally, this resulting in wetting of the adjacent component and thus resulting in a materially integral adhesive connection upon cooling.

Various plastics materials can be used as materials leads the functional element as well as for any potential plastic finish of the cover element or the plastics-material intermediate layer, said plastics materials being for example polyurethane, polyethylene, polyvinylchloride, or polyamide, wherein the functional element can also be embodied as a part with two or three components, for example. The list of the plastics materials used is not exhaustive.

In this case the functional element in particular, or else the cover element, can have a color that is different from that of the main panel. This can serve for design purposes, on the one hand, but can also serve for indicating an item of information, for example in terms of the stiffness of a functional element serving as a stabilizing element. For example, if the functional element in the form of a stabilizing stiffener is embodied in green, this would be a softer stabilizing element than a stabilizing element embodied in red, for example, while a stabilizing element embodied in dark blue would be the hardest, for example.

The textile part per se can be of the most varied type. Said textile part can be a bandage, an orthotic, or a stocking, in particular a compression stocking or compression arm hosiery, wherein this list is not exhaustive. A functional element of various type or geometry, respectively, for example an elongate or curved rod-type functional element, a joint-type functional element, a functional element configured as a belt loop, a functional element configured as a traction aid which can be manually gripped, thus configured as a dressing aid, or a functional element configured as a pad, can be disposed on the bandage, the orthotic, or the stocking. The most varied functional elements can thus be used, wherein this list is also not exhaustive. The shape, or the geometry, respectively, of the cover element and optionally also of the slot that is provided on the cover element will then be designed depending on the type or geometry, respectively, of the functional element.

It is preferable herein for the functional element and thus also the cover element to be disposed on the external side of the textile main panel. It is however likewise possible for the functional element and the cover element to be placed on the internal side of the main panel.

Besides the textile part per se, the invention furthermore relates to a method for producing such a textile part, said method being distinguished in that at least one functional element from plastics material as well as at least one cover element which engages only in portions across the main panel as well as the functional element are disposed on a textile main panel, whereupon a materially integral connection between the functional element and the main panel is established by an input of energy.

It can furthermore be provided that a materially integral connection is established between the functional element and the main panel as well as between the cover element and the functional element and/or the main panel by an input of energy.

Accordingly, a materially integral connection is not only established between the functional element and the main panel, but also for fastening the cover element of the functional element, to the main panel, or to both. Materially integral connections thus take place exclusively among the components. This has the particular advantage that all of the fastenings can be generated in a single process step by a single input of energy, for example in the form of high-frequency or ultrasonic vibrations, in the context of a plastics-material welding method.

It can furthermore be provided that either the functional element is fused in the region of the engagement of the cover element in order for the connection to the cover element and to the main panel to be established, or that the cover element per se, or a coating provided on the cover element, or an intermediate tier incorporated between the cover element and the functional element and/or the main panel, on the one hand, as well as the functional element, on the other hand, are/is fused for establishing the connection of the cover element to the functional element and/or to the main panel, and of the functional element to the main panel. Different variants for connecting the individual elements to one another are thus possible, this depending in particular on whether or not the cover element per se is provided with a corresponding content of plastics material which is at least in part fusible and by way of which a materially integral connection to the main panel/functional element is able to be established.

A cover element from a preferably hook-and-loop capable textile, in particular of a velour, alternatively also a plastic film is preferably used as the cover element per se. Independently thereof, the cover element is preferably flexible, this being the case in the case of a textile and of a correspondingly thin plastic film, this enabling the cover element to be able to replicate, or jointly carry out, respectively, corresponding geometric deformations of the main panel or of the functional element, respectively.

A main panel in the form of a knitted panel, in particular a compressive knitted panel, is preferably used as the main panel.

Finally, a functional element as well as optionally a coating, or a finish, respectively, of the cover element or an intermediate layer or a cover element per se from polyurethane, polyethylene, polyvinylchloride, or polyamide is preferably used.

The various features of novelty which characterize the invention are pointed out with particularity in the claims annexed to and forming a part of the disclosure. For a better understanding of the invention, its operating advantages, specific objects attained by its use, reference should be had to the drawings and descriptive matter in which there are illustrated and described preferred embodiments of the invention.

DETAILED DESCRIPTION OF THE INVENTION

Figure 1:
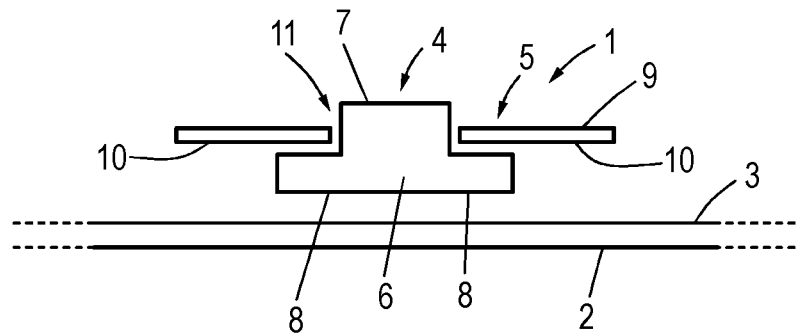
FIG. 1 shows an exploded view of a textile part according to the invention in a partial view, having a main panel, a functional element, and a cover element, prior to said functional element and said cover element being fastened to the main panel.

FIG. 1 shows an exploded view of a textile part 1 according to the invention, comprising a textile main panel 2 in the form of a knitted panel, in particular a compressive knitted panel. A combination of a functional element 4 and the cover element 5 is to be applied and fastened to the external side 3 of said compressive knitted panel, wherein a materially integral connection of the functional element 4 to the external side 3 of the main panel, on the one hand, but also, on the other hand, a materially integral connection of the cover element 5 to the functional element 4, on the one hand, and also to the external side 3 of the main panel, on the other hand, is to take place in the exemplary embodiment described.

Figure 2:
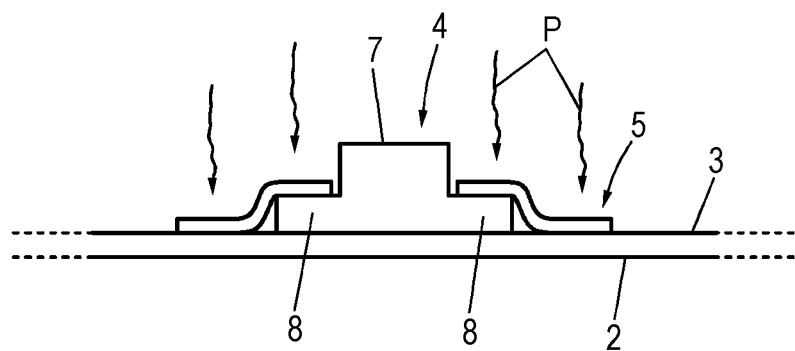
FIG. 2 shows the assembly from FIG. 1 having the functional element and the cover element applied to the main panel while said functional element and said cover element are being fastened.

For this purpose, the functional element 4 and the cover element 5 are placed onto the external side 3 of the main panel 2, see FIG. 2. The functional element in the exemplary embodiment shown is T-shaped, thus having a wide transverse leg 6 and a longitudinal leg 7 which projects from said transverse leg 6. The functional element 4 by way of the transverse leg 6 bears on the external side 3. The lateral fastening portions 8 which project from the longitudinal leg 7 serve for connecting the functional element 4 to the main panel 2, on the one hand, but also for connecting the cover element 5 to the functional element 4 on the other side of the connection, on the other hand. The cover element 5 is preferably a flexible element, in particular a textile, preferably a velour. Said cover element 5 thus has a textile portion 9, a plastics-material coating 10 being laminated on the lower side of the textile portion 9 in the example shown; that is to say that the cover element 5 is equipped with a content of plastics material which can be fused, this yet to be discussed hereunder.

Instead of a coating 10 which is fixedly laminated to the textile panel 9, a separate intermediate tier which is formed by way of a plastic film can also be provided, that is to say that the component identified by the reference sign 10 in FIG. 1 can also be a separate plastics-material intermediate tier which is not fixedly connected to the cover element 5 but can likewise be fused and can establish the corresponding connections, as is described hereunder. Besides, the cover element 5 can of course also be embodied in the form of a plastic film per se which can be fused.

The cover element 5 per se is embodied so as to be rectangular/elongate, so to speak, and has a centric elongate slot 11 which is penetrated by the longitudinal leg 7, see FIG. 2, said longitudinal leg 7 thus protruding somewhat from the cover element 5. The cover element 5 by virtue of the rectangular design embodiment thereof thus borders the projecting longitudinal web 7 on all sides (to this end see also FIG. 7).

The connection between the functional element 4 and the cover element 5 as well as the knitted part 2 takes place by an input of energy in that radiation energy, as is illustrated by the arrows P in FIG. 2, is applied in the form of high-frequency or ultrasonic radiation. This means that high-frequency or ultrasonic welding takes place.

This leads to the functional element 4 in the region of the fastening portions 8 thereof fusing on both sides, on the one hand, as well as the plastics-material coating 10 of the covering element 5 fusing. Wetting of the fused plastic-material masses on the functional element 4 and on the cover element 5 arises on the one hand, said functional element 4 and said cover element 5 connecting in a materially integral manner, as well as wetting of the knitted panel 2 on the external side on account of the fused plastics-material coating 10, on the other hand. Corresponding materially integral connections result upon cooling, as is indicated by the undulated lines in FIG. 3, specifically first materially integral connections 12 between the functional element 4 and the main panel 2 on the external side 3 of the latter, on the one hand, and materially integral connections 13 between the functional element 4 and the cover element 5 in the region of the engagement of the latter across the fastening portions 8, on the other hand, and finally materially integral connections 14 between the cover element 5 and the main panel 2 on the external side 3 of the latter.

As can be seen, all of the materially integral connections 12, 13, 14 are configured in a single process step by a single input of energy; this means that all elements can be connected to one another in a single process step.

The functional element 4 per se is from plastics material, preferably from polyurethane, polyethylene, polyvinylchloride, or polyamide, wherein this list is not exhaustive. The same materials can also be used for the laminated coating 10 of the cover element 5.

Figure 4:
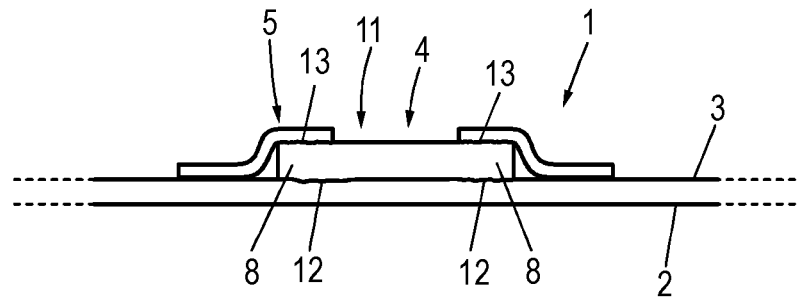
FIG. 4 shows a partial view of a textile part according to the invention of a second embodiment, having a cover element fastened only to the functional element.

FIG. 4 shows an exemplary embodiment of a knitted part 1 according to the invention having a functional element 4 and a cover element 5 fastened thereto. The materially integral connections established here are likewise generated by high-frequency or ultrasonic welding. Implemented on the one hand are the materially integral connections 12 of the functional element 4 to the main panel 2, thus to the knitted panel. Moreover, materially integral connections 13 between the functional element 4 and the cover element 5 are implemented in the region of the fastening portions 8 of the functional element 4. Here the functional element 4 lies loosely above the main panel 2, that is to say that the cover element 5 and the main panel 2 are not fixedly connected to one another.

The cover element 5 in this design embodiment of the invention does not have to be equipped with a coating 10 since the local fusing of the functional element 4 in the region of the fastening portions 8 alone is sufficient for connecting said cover element 5 and said functional element 4 to one another in a materially integral manner.

As is shown in FIG. 4, the functional element 4 here is configured as an I-shaped, thus planar, stabilizing stiffener, so to speak, which lies below the through-hole 11, thus neither engaging in the latter nor penetrating the latter.

Figure 5:
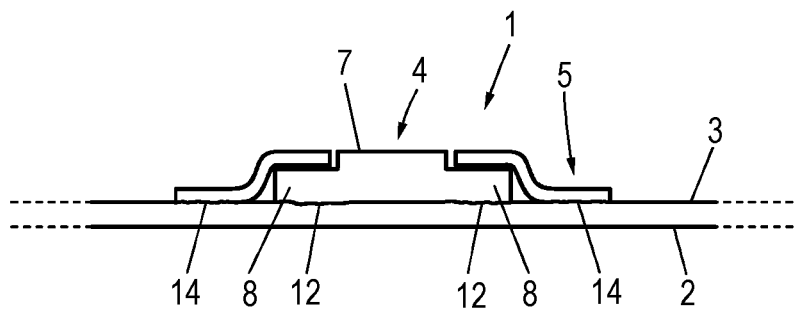
FIG. 5 shows a partial view of a textile part according to the invention of a third embodiment, having a cover element fastened only to the main panel.

FIG. 5 shows a further design embodiment of the textile part 1 according to the invention. The functional element 4, the cover element 5, as well as the main panel 2 to which the functional element 4 by way of the connections 12 is again fastened in a materially integral manner by melting are again provided here. In this design embodiment, the cover element 5 is again provided with a corresponding plastic finish, for example in the form of the coating 10, which enables the materially integral melt connections 14 to be established between the cover element 5 and the main panel 2. However, the cover element 5 lies loosely on the functional element 4, or on the fastening portions 8, respectively, no connection thus being provided here. The cover element 5 in this design embodiment of the invention is only peripherally provided with the coating 10 but not in the region toward the overlap with the functional element 4, for example.

The functional element 4 again shows a somewhat different cross-sectional geometry. Said functional element 4 here indeed also has a longitudinal leg 7, said longitudinal leg 7 however being very short such that the latter ultimately runs so as to be flush with the cover element 5.

Figure 6:
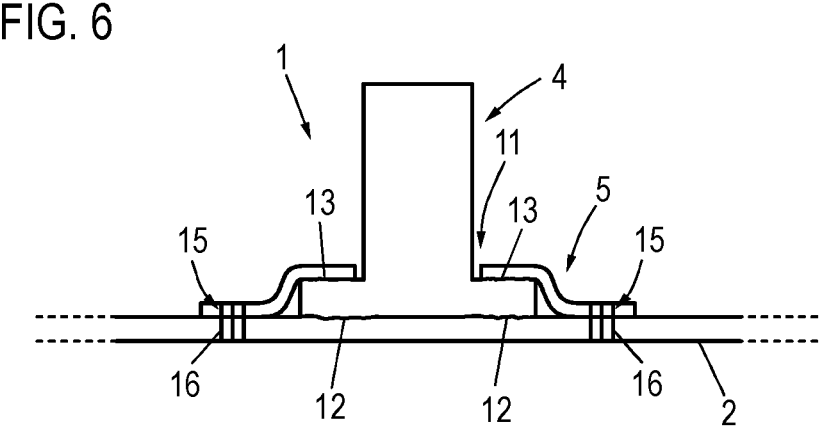
FIG. 6 shows a schematic illustration of a textile part according to the invention, having a cover element fastened in a form-fitting manner to the main panel by sewing, and a cover element welded to the functional element.

FIG. 6 shows a fourth variant of the invention of a textile part 1 according to the invention. The functional element 4 as well as the cover element 5 and the main panel 2 are again provided. The plastics-material functional element 4 by way of the materially integral connections 12 is again connected to the main panel 2 by high-frequency or ultrasonic welding. The cover element 5 is likewise connected to the functional element 4 by way of materially integral connections 13, wherein the latter are established by locally fusing the fastening portions 8 on the surface thereof, that is to say that the cover element 5 is not equipped with a corresponding plastics-material coating 10. Two materially integral connections 12, 13 which lie on top of one another, so to speak, are also implemented here.

The cover element 5 is furthermore peripherally connected to the main panel 2, this however being by way of the form-fitting connection 15 which here are established by sewing using a sewing thread 16. All three elements are again fixedly connected to one another here.

In this design embodiment of the invention, the functional element 4 by way of a relatively long longitudinal leg 7 extends far from the through-hole 11 of the cover element 5. The longitudinal leg 7 can be provided with a through-hole, for example, such that said longitudinal leg 7 is embodied in the manner of the handle, so to speak, and can be manually gripped and serve as a dressing aid, to which end said longitudinal leg 7 is fastened to a stocking or the like which forms the basic knitted fabric, for example.

Figure 3:
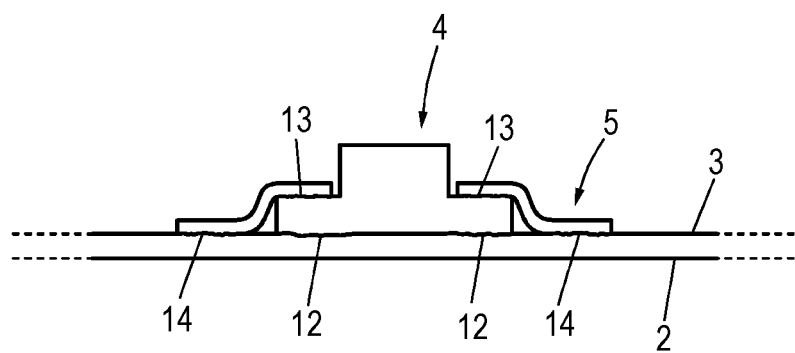
FIG. 3 shows the assembly of the functional element and the cover element being connected to the main panel by welding.
Figure 7:
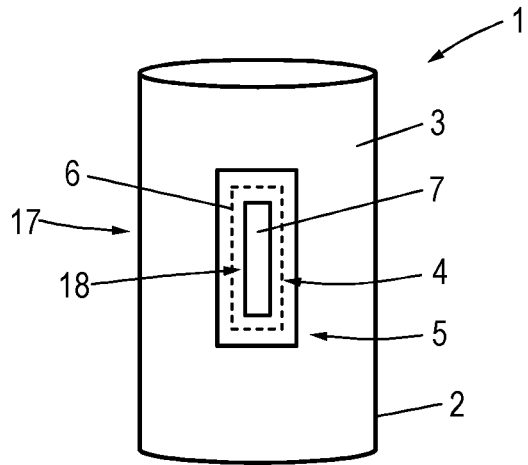
FIG. 7 shows a schematic illustration of a textile part according to the invention in the form of a bandage having a rod-shaped functional element.

FIG. 7 shows a schematic illustration of a first specific design embodiment of a textile part 1, here in the form of a bandage 17. Shown is the main panel 2 which, as is commonplace in a bandage, is tubular here. The functional element 4 is fastened to the external side 3 of the main panel, on the one hand; the cover element 5 is also disposed thereon, on the other hand. The functional element 4 here is embodied as an elongate stabilizing stiffener 18 which in the cross section is T-shaped, for example, as is illustrated in FIGS. 1 to 3. The transverse leg 6 is shown in dashed lines, on the one hand, while the longitudinal leg 7 which exits from the through-hole 11 of the cover element 5 is likewise illustrated. All variants of connections described above are conceivable for this design embodiment.

Figure 8:
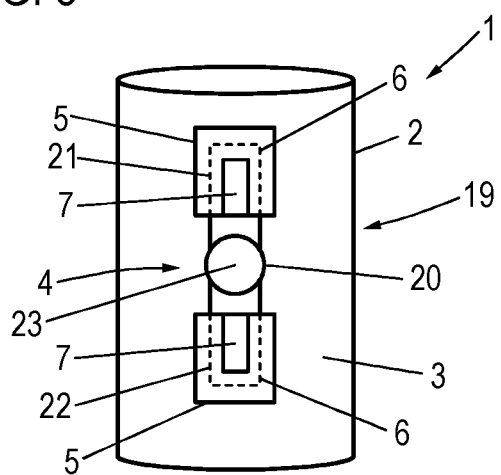
FIG. 8 shows a schematic illustration of a textile part according to the invention in the form of an orthotic, having a functional element in the form of a joint.

FIG. 8 shows a second specific design embodiment of the invention of a textile part 1 according to the invention, here in the form of an orthotic 19 again comprising a main panel 2, the functional element 4 here in the form of the joint 20 being disposed on the external side 3 of said main panel 2. The joint 20 has two legs 21, 22 which are connected to one another by way of an articulated connection 23. Each leg 21, 22 is in portions engaged across by a separate cover element 5. Here too, each articulated leg 21, 22 again has a corresponding transverse leg 6, here shown in dashed lines, as well as a longitudinal leg 7 which penetrates the corresponding through-hole 11 which is proximal to the cover element, while the articulated connection 23 is exposed. Here too, all of the different variants of fastening the elements to one another as described above are conceivable.

In the case of this design embodiment of the invention there is also the possibility, for example, proceeding from the fastening variant according to FIG. 6, of first sewing the two cover elements 5 to the main panel 2 by way of the form-fitting connection 16, but for running the scene only about three sides such that the mutually facing element sides are not sewn but open on one side such that the articulated legs 21, 22 here can be pushed into these pocket-shaped cover elements 5, the welded connection between the functional element 4 and the main panel 2 as well as between the cover element 5 and the functional element 4 being able to be established only thereafter.

Figure 9:
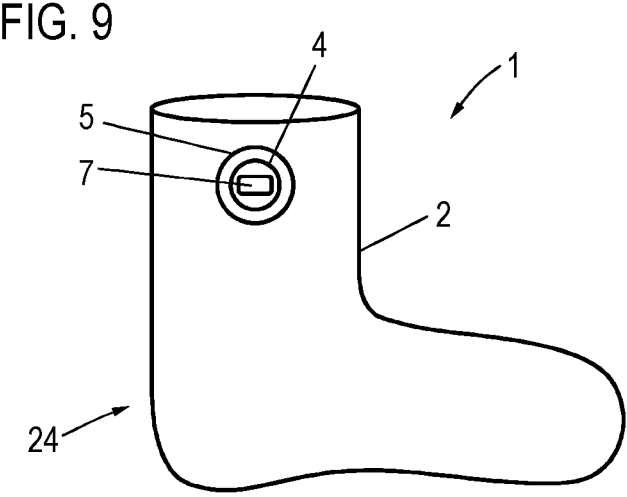
FIG. 9 shows a schematic illustration of a textile part according to the invention in the form of a stocking, having a functional element which is embodied as a handle which is to be manually gripped and which serves as the dressing aid.

FIG. 9 finally shows a third specific variant of the invention of a textile panel 1 having a main panel 2 in the form of a stocking 24. The functional element 4 and the cover element 5 are again disposed in the region of the upper stocking 24, wherein the functional element 4 here is round/disk-shaped, so to speak, and has a longitudinal leg 7 which projects relatively far and which penetrates the corresponding through-hole in the cover element 5, said through-hole here also being embodied so as to be round. This herein is a handle, for example, as has already been described in the context of FIG. 6. Here too, the corresponding variants of fastening are conceivable, wherein the variants in which the cover element 5 is connected to the functional element 4 as well as to the knitted panel 2 are preferable herein by virtue of the forces acting when pulling upward.

While specific embodiments of the invention have been shown and described in detail to illustrate the inventive principles, it will be understood that the invention may be embodied otherwise without departing from such principles.

I claim:

1. A textile part, in particular a textile orthopedic aid, comprising a textile main panel as well as at least one functional element from plastics material which is disposed on the textile main panel, wherein the at least one functional element has a laterally projecting fastening portion, wherein at least one planar cover element which engages across the laterally projecting fastening portion of the at least one functional element disposed on the textile main panel and which also extends across the textile main panel is provided, wherein the at least one planar cover element is materially integrally fused to the textile main panel and to the laterally projecting fastening portion of the at least one functional element so that material of the at least one planar cover element intermingles with material of the textile main panel and material of the laterally projecting fastening portion, and only the laterally projecting fastening portion of the at least one functional element is materially integrally fused to the textile main panel so that the material of the laterally projecting fastening portion intermingles with the material of the textile main panel.

2. A textile part according to claim 1, wherein the at least one planar cover element has a through-hole, wherein the at least one functional element runs behind the through-hole, or wherein the at least one planar cover element runs so as to be flush with the at least one functional element engaging in the through-hole, or wherein the at least one functional element penetrates the through-hole.

3. A textile part according to claim 2, wherein the laterally projecting fastening portion is connected to the textile main panel by way of said at least one planar cover element, wherein a raised portion of the at least one functional element that adjoins the laterally projecting fastening portion extends into or through the through-hole.

4. A textile part according to claim 1, wherein the at least one planar cover element has a fused coating, or wherein a fused intermediate tier is provided between the at least one planar cover element and the at least one functional element and/or the textile main panel.

5. A textile part according to claim 1, wherein the at least one planar cover element per se is composed of or contains a fusible material.

6. A textile part according to claim 1, wherein the at least one planar cover element is a hook-and-loop capable textile or a coated plastic film.

7. A textile part according to claim 1, wherein the textile main panel is an in particular compressive knitted panel.

8. A textile part according to claim 4, wherein the at least one functional element, as well as optionally a coating, or the fused intermediate tier or the at least one planar cover element, is made from polyurethane, polyethylene, polyvinylchloride, or polyamide.

9. A method for producing a textile part comprising a textile main panel as well as at least one functional element from plastics material which is disposed on the textile main panel, wherein the at least one functional element has a laterally projecting fastening portion, wherein at least one planar cover element which engages only across the laterally projecting fastening portion of the at least one functional element disposed on the textile main panel and which also extends across the textile main panel is provided, wherein the at least one planar cover element is materially integrally fused to the textile main panel and to the laterally projecting fastening portion of the at least one functional element so that material of the at least one planar cover element intermingles with material of the textile main panel and material of the laterally projecting fastening portion, the method comprising the steps of: disposing the at least one functional element from plastics material as well as the at least one planar cover element which engages only across the textile main panel as well as the at least one functional element on the textile main panel; materially integrally fusing the at least one planar cover element to the textile main panel and to the laterally projecting fastening portion of the at least one functional element so that the material of the at least one planar cover element intermingles with the material of the textile main panel and material of the laterally projecting fastening portion; and materially integrally fusing only the laterally projecting fastening portion of the at least one functional element to the textile main panel by an input of energy so that the material of the laterally projecting fastening portion intermingles with the material of the textile main panel.

10. The method according to claim 9, wherein the at least one functional element is fused in a region of the engagement of the at least one planar cover element in order for a connection to the at least one planar cover element to be established, or the at least one planar cover element per se, or a coating provided on the at least one planar cover element, or an intermediate tier incorporated between the at least one planar cover element and the at least one functional element.

11. The method according to claim 10, wherein the at least one planar cover element is made from a hook-and-loop capable textile or from a plastic film, and/or the textile main panel is a compressive knitted panel, and/or the at least one functional element as well as optionally a coating of the at least one planar cover element, the intermediate tier or the at least one planar cover element per se is made from polyurethane, polyethylene, polyvinylchloride, or polyamide.

* * * * *